(12) United States Patent
Allison et al.

(10) Patent No.: US 12,036,367 B2
(45) Date of Patent: Jul. 16, 2024

(54) AIRWAY AND EYE TAPING SYSTEM AND METHOD OF ITS USE

(71) Applicants: Cory Allison, Chattanooga, TN (US);
Kelly Good, Chattanooga, TN (US)

(72) Inventors: Cory Allison, Chattanooga, TN (US);
Kelly Good, Chattanooga, TN (US)

(73) Assignee: Kelcor, LLC, Chattanooga, TN (US)

( * ) Notice: Subject to any disclaimer, the term of this patent is extended or adjusted under 35 U.S.C. 154(b) by 613 days.

(21) Appl. No.: 17/336,747

(22) Filed: Jun. 2, 2021

(65) Prior Publication Data

US 2021/0379315 A1    Dec. 9, 2021

Related U.S. Application Data

(60) Provisional application No. 63/035,209, filed on Jun. 5, 2020.

(51) Int. Cl.
*A61M 16/00* (2006.01)
*A61M 16/04* (2006.01)
*A61M 16/06* (2006.01)

(52) U.S. Cl.
CPC .... *A61M 16/0688* (2014.02); *A61M 16/0497* (2013.01)

(58) Field of Classification Search
CPC .......... A61M 16/0688; A61M 16/0683; A61M 16/0497; A61M 16/0488; A61M 16/0461; A61F 9/04
See application file for complete search history.

(56) References Cited

U.S. PATENT DOCUMENTS

| 2008/0173310 | A1* | 7/2008 | Marcoe | A61M 16/0497 |
| | | | | 128/207.17 |
| 2016/0100985 | A1* | 4/2016 | Kennedy | A61F 9/04 |
| | | | | 128/858 |
| 2019/0381267 | A1* | 12/2019 | De Oliveira | A61M 16/0497 |

FOREIGN PATENT DOCUMENTS

WO    WO-2020109775 A1 *  6/2020  ........ A61M 16/0497

* cited by examiner

*Primary Examiner* — Michael R Reid
*Assistant Examiner* — Sarah B Lederer
(74) *Attorney, Agent, or Firm* — Miller & Martin PLLC

(57) ABSTRACT

An airway holder for use in holding an airway device, such as an air or nose tube, has a first pair of wings symmetrically disposed about a center portion and a second pair of wings asymmetrically disposed about the center portion. One of the wings of the second pair of wings has an offset to facilitate that wing wrapping about a portion of the other wing of that pair about the airway device, before then, preferably being adhered to the face of the patient. The airway holder may be provided as a portion of a kit with eye protectors in an effort to remove surgical tape (and subsequent reuse with other procedures to potentially spread contamination).

19 Claims, 4 Drawing Sheets

AIRWAY AND EYE TAPING SYSTEM AND METHOD OF ITS USE

CLAIM OF PRIORITY

This application claims the benefit of U.S. Provisional Application No. 63/035,209 filed Jun. 5, 2020, which is incorporated herein by reference in its entirety.

FIELD OF THE INVENTION

The present invention relates to a kit and portions thereof for connecting self-adhering tape or bandages to the body of a person, and more particularly, to such a system which provides for an airway adhesive anchor having a first adhesive portion connecting to a medical implement, then a second adhesive portion and then preferably connected to the patient (such as cannulas, endotracheal tubes, laryngeal mask airways, etc. and/or other medical devices) as will be explained herein, preferably, along with a pair of eye tape, preferably provided in kit form.

BACKGROUND OF THE INVENTION

Supporting endotracheal tubes has been done in the prior art with various devices. In many instances, in short term airway management, medical professionals utilize adhesive tape rolls for securing airway tubes to the patient's body. The tape is often unrolled and stuck to a first cheek, wrapped about the device several times, stuck to the other cheek, and ripped from the roll. Furthermore, a single roll of tape may be utilized on more than one patient. It is possible that bodily fluid can be in contact with the tape during the application process and potentially provide a way to transfer germs from one patient to another inadvertently in the operating room or other patient care settings (ER, ambulance, etc.) increasing the risk of healthcare acquired infections.

In an effort to overcome such disadvantages of tape rolls, U.S. Published Patent Application 2010/0199997 shows a tracheal tube support apparatus. This design could support an endotracheal tube and/or laryngeal mask airway. Other efforts to provide endotracheal tube retainer include U.S. Pat. No. 4,326,515 which provide a particularly substantial structure, but not one particularly inexpensive to manufacture. U.S. Pat. No. 5,743,885 shows a specialty bandage, which also appears to adhere to the tube with adhesive like U.S. Published Patent Application No. 2010/0199997 and others, such as U.S. Pat. No. 5,221,265.

Accordingly, numerous efforts have been made to address the problem of tape rolls utilized on successive patients, or provide specialty tube supports, but none are known to have been widely adapted in the medical field. There appears to be a need for clean, universal, single use, short term airway taping system for securing medical components to the body of a person.

Another need exists for a kit of an airway retention device together with a pair of eye tape patches provided in kit form for use by medical personnel for closing and protecting the patient's eyes when unconscious/loss of lid reflex.

OBJECT OF THE INVENTION

It is an object of many embodiments of the present invention to provide an improved method of securing medical components to the body of a person.

It is another object of many embodiments of the present invention to provide an improved method of securing medical components to the body of a person with an advantageous airway securing device, possibly in a kit form possibly with eye patch tape.

It is another object of many embodiments of the present invention to provide an improved device for and/or method of connecting medical components to the body of an individual while securing the component to the body of the person in an improved manner.

It is yet another object of many embodiments to provide an improved eye patch tape possibly in a kit to allow an improved method of closing the eye in application.

Accordingly, in accordance with a presently preferred embodiment of the present invention, a kit of a presently preferred embodiment of the present invention may provide a first pair of wings connected to a second pair of wings at a center or connector portion. The first and second pair of wings may each have possibly a planar adhesive surface for connecting to the skin of a patient preferably connected at the center portion. The first and second pairs of wings are each often planar and can be applied to conform to the shape of the skin, like an adhesive tape. The first pair of wings connect to the second pair of wings with a center or connector portion. Some suitable materials can include Medipore™, Durapore™, Micropore™ and many other medical style tape constructions.

A second pair of wings can be provided initially above (or below) the first pair of wings and can be configured to wrap about, if not around, an airway device, preferably before then being directed to contact the face of the patient. The second pair of wings may preferably be a similar or dissimilar material as the first pair of wings. The first pair of wings may be symmetrically disposed about the center, but for many preferred embodiments, the second pair of wings are asymmetrically provided relative to the center portion.

Accordingly, the medical device can be connected at the center by first removing a liner portion at the center portion. The first pair of wings can then be anchored to the face. The second pair of wings can then be wrapped about, if not around, the medical device. The second wing of the second pair of wings is preferably provided with an offset so as to be displaced relative to the first wing of the second pair of wings to assist in wrapping around the medical device and/or the first wing of the second pair of wings and then be directed over the face and/or wing of the first pair of wings to thus anchor the medical device in place relative to the face of a patient.

In addition to the airway taping system being an improvement, the airway holder also may be provided as part of a kit particularly with the endotracheal tube embodiment, possibly together with pre-formed eye patches which could have adhesive on one side covered by release paper so as to be quickly installed and/or removed by a medical professional. The eye patch may be adhered to cover the eye of the patient so as to protect the eyes during a surgical operation or when otherwise unconscious. Eye patches may have top and/or bottom tabs to assist in installation/removal. The bottom tab, if utilized, may be located toward the bottom of the eye lid when installed, and may be particularly useful in installing the eye patch, while the top tab, if utilized, may be located near the top of the eye lid when installed, and may be particularly helpful in removing the eye patch so as to grasp and remove in a downward motion (so as to not inadvertently irritate a patient's eye during application or removal).

In such a scenario, no tape roll is preferably utilized to potentially spread germs to, or from, another patient, and no other taping system in the market is currently available to cover the range of various airway devices such as endotracheal, supraglottic, etc.

BRIEF DESCRIPTION OF THE DRAWINGS

The particular features and advantages of the present invitation will become apparent from the following description when considered in conjunction with the accompanying drawings in which.

DETAILED DESCRIPTION OF THE INVENTION

Figure 1:
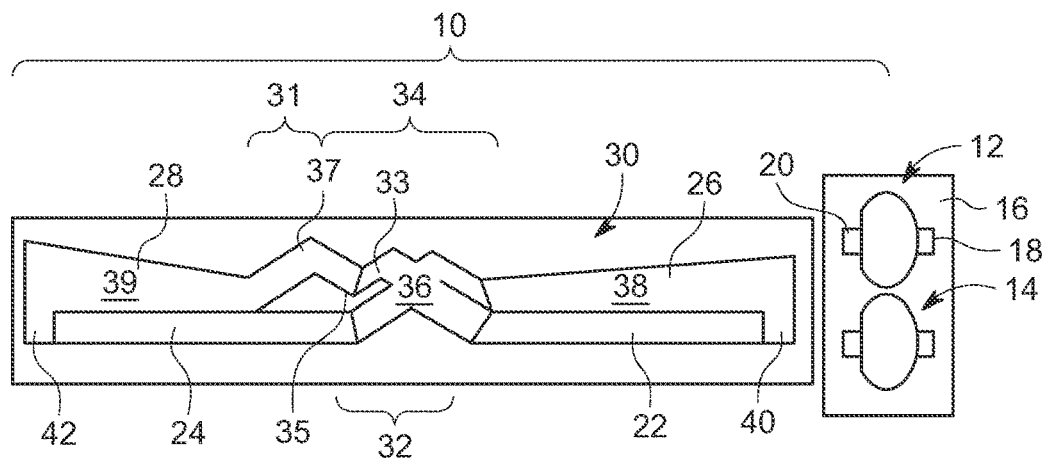
FIG. 1 is a back plane view, the liner side, of a presently preferred embodiment of the present invention showing a kit having eye tape patches and an airway tape support of a presently preferred embodiment of the present invention.

FIG. 1 shows a kit 10 of a presently preferred embodiment of the present invention having a first and second eye patches 12,14 connected to release paper 16. It is understood that each of the eye patches 12,14 could be connected to separate release papers 16 in other embodiments. The first and second eye patches may have tabs 18,20 and/or others to assist in attaching/detaching the eye patches 12,14 to patient and/or pulling the eye patches 12,14 away from the release paper(s) 16 so as to be able to apply to protect the eyes of a patient.

Figure 3:
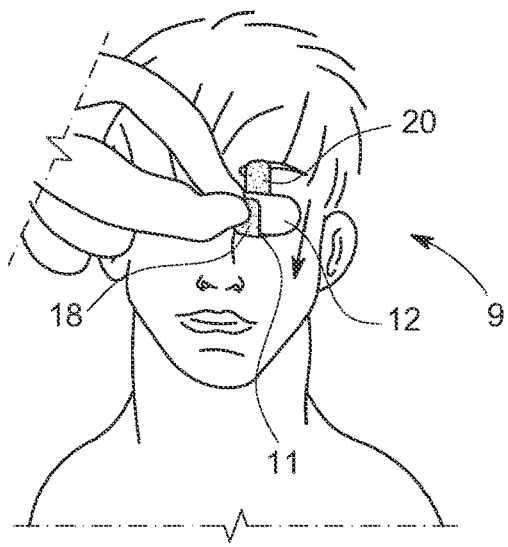
FIG. 3 is a perspective view showing the eye patch of FIG. 1 being installed on a patient.

When provided in kit form as a kit 10, it is anticipated that the eye patches 12,14 may be removed from the release paper 16 and then applied to the eyes 11,13 of the patient 9 normally from the top to the bottom of the eye possibly with tab 18 so as to ensure that the eyes are protected and closed during the application process to protect the patient's eyes. The top portion of eye patches 12,14 is preferably tending towards planar and may be installed below an eyebrow so as not to grab the eyebrow (when in place on the patient). Removal of the eye patches 12,14 is typically also done from the top down over the eye. FIG. 3 shows the patch 12 being applied with tab 18 with an upper portion off the patch 12 on the eye lid of the patient 9 and applying downwardly as shown. Removal may preferably involve grasping tab 20 and pulling downwardly as well to maintain eye closure.

Other eye patches may be able to be provided in kit 10 with the airway holder 30 of the presently preferred embodiment of the present invention. Eye patches 12,14 and the method of installation/removal may be novel on their own. Eye patches 12,14 may be in kits 10, other kits, or separately on their own.

Additionally, the airway holder 30 may be provided with eye patches 12,14 in kits 10, other kits, or separately. The airway holder 30 preferably provides a first pair of wings 32 comprised of first and second wings 22,24 and a second pair of wings 34 comprised of third and fourth wings 26,28. First pair of wings 32 may be constructed in a plurality of different ways. First, first pair of wings 32 could be provided in strip form as illustrated, possibly having first and second wings 22,24. Second pair of wings 34 are preferably a different construction and connect to the first set of wings 32 at a portion such as center portion 36. In fact, for many embodiments, first pair of wings 32 may be symmetrically disposed about center portion 36 while second pair of wings 34 may be asymmetrically disposed about center portion 36 for at least some embodiments.

Specifically, fourth wing 28 may start extending away from center portion 36 somewhat similarly as third wing 26, but instead of then continuing to transition into leg 39, the fourth wing preferably has an offset 31 with arm 33 bending upwardly at elbow 35 and then downwardly at shoulder 37 to then transition to leg 39 possibly similarly to leg 38. Both legs 38,39 may have feet 40,42 which can assist as may be described below, for at least some embodiments.

Figure 2:
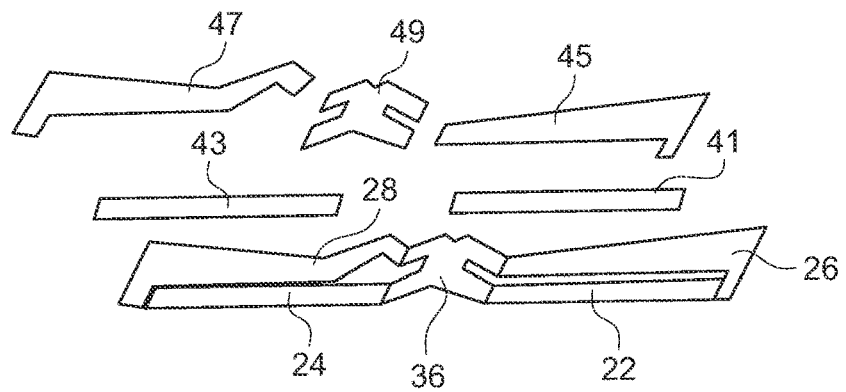
FIG. 2 is a rear exploded view of the airway support of FIG. 1.

FIG. 2 shows release paper segments 41,43,45,47,49 removed from each of the wings 22,24,26,28 as well as the center portion 36. Other embodiments may have different release paper segments 41,43,45,47,49, but this construction can assist in connection for at least some embodiments as will be described in further detail below.

Various embodiments may have other configurations for the first and second pair of wings 32,34 The second pair of wings 34 could be connected to the first pair of wings 32 potentially at center 36 or other location.

Figure 4:
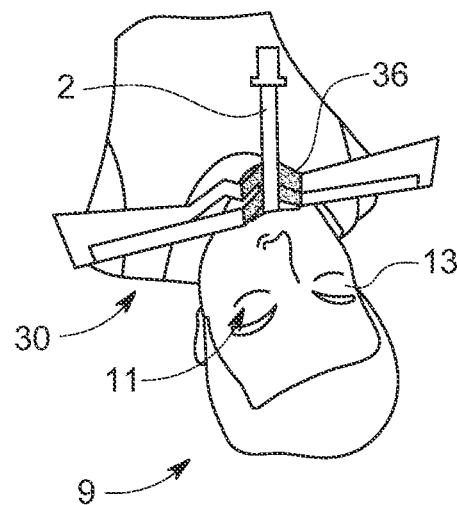
FIG. 4 is a perspective view showing an early installation step of the airway support shown in FIG. 1.

For a preferred method of installation for at least some embodiments, such as the embodiment illustrated, the center liner portion 49 can be removed and the airway holder 30 can be attached at the center portion 36 to the tube or airway device, such as is illustrated in FIG. 4 as an endotracheal tube 2 inserted into the patient 9. Other airways which could benefit from an airway holder 10 include, but are not limited to, laryngeal mask airway, nasal endotracheal tube, double lumen endotracheal tube, oral RAE endotracheal tube, nasal RAE endotracheal tube, and/or other tube inserted into a body cavity such as an airway directed to the lungs.

Figure 5:
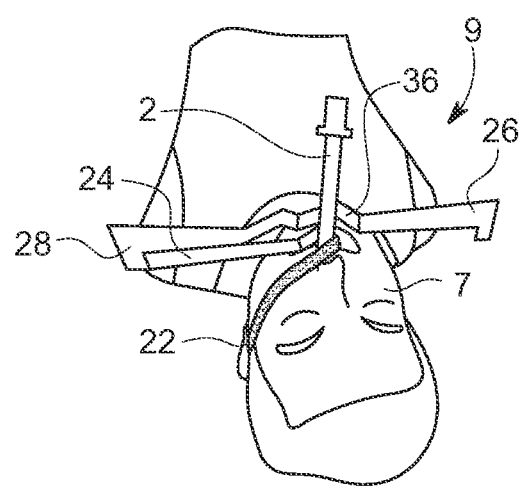
FIG. 5 is a perspective view showing another installation step of the airway support shown in FIG. 1.
Figure 6:
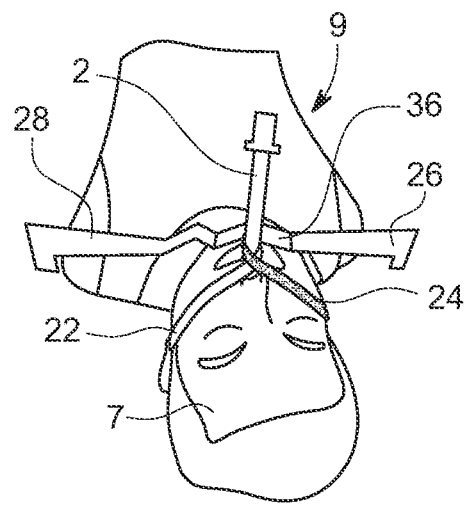
FIG. 6 is a perspective view showing another installation step of the airway support shown in FIG. 1.
Figure 7:
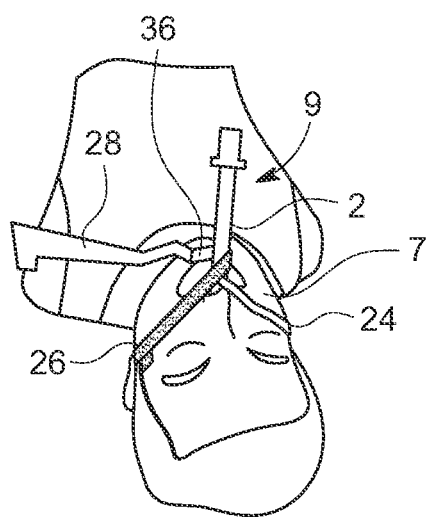
FIG. 7 is a perspective view showing another installation step of the airway support shown in FIG. 1.
Figure 8:
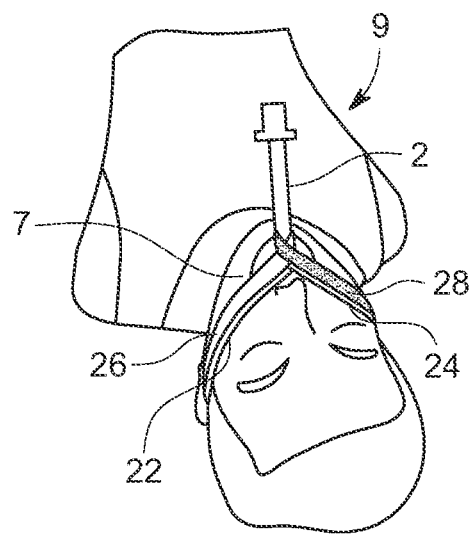
FIG. 8 is a perspective view showing the airway support shown in FIG. 1 fully installed on an endotracheal tube on a patient.
Figure 9:
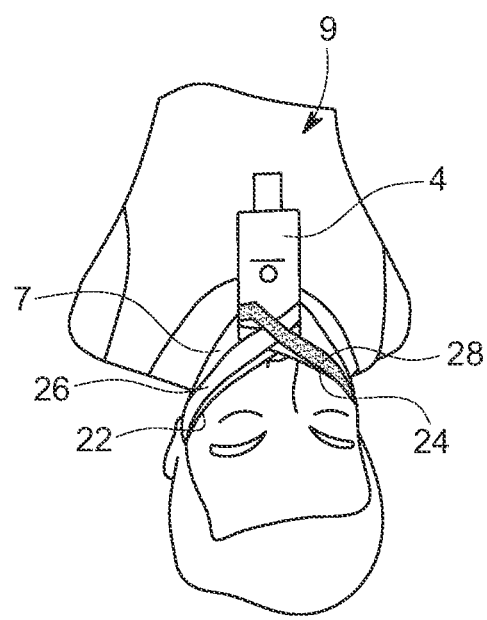
FIG. 9 is a perspective view showing the final installation step of the airway support shown in FIG. 1 wrapped about a supraglottic airway instead of an endotracheal tube.

FIG. 5 shows the liner portion 41 is removed from the first wing 22 and the first wing 22 can then be directed about the tube 2 on to the face 7. Then the liner portion 43 is removed from the second wing 24, if not already removed, and the second wing 24 can be directed about the tube 2 and onto the face 7 as is shown in FIG. 6. The third wing 26 can have its liner portion 45 removed, if not already removed, and it can be directed about and/or around the tube 2 onto the face 7 and/or onto the first wing 22 as is shown in FIG. 7. Finally, the fourth wing 28 can have its liner portion 47 removed, if not already removed, and it can wrap completely around the tube 2 and then onto the face 7 and/or onto the second wing 24 as is shown in FIG. 8. The offset 31 is helpful to allow the fourth wing 28 to go over the third wing 26 without interference for at least some embodiments. FIG. 9 shows the airflow holder 30 supporting a supraglottic airway 4 instead of an endotracheal tube 2. For this embodiment, wrapping the fourth wing 28 around the supraglottic airway 4 may not be necessary for all embodiments, and the fourth wing 28 might be directed about the supraglottic airway 4 and be attached to face 7 sufficiently thereto. Fully installed airway holder 30 on an endotracheal tube 2 is shown in FIG. 8 and fully installed airway holder 30 on a supraglottic airway 4 is shown in FIG. 9.

The first and second pair of wings 32,34 may be a medical adhesive tape type material or other appropriate material. This particular construction has been found to work well with endotracheal tubes 2 and supraglottic airways 4. Other embodiments may have other shapes such as for retaining lines, cannulas, pain pumps and/or other medical devices to the body of a patient. Eye patches 12,14 may be made of a similar or dissimilar type of material.

The airway holder 30 may be used to secure the airway by wrapping at least one wing 26,28 of the pair of wings 34 around the airway. The airway holder 30 works well on several categories of airways: oral endotracheal tubes (includes regular double lumen, oral RAE endotracheal tubes, etc.), supraglottic airways (includes laryngeal mask airways, iGels, etc.), nasopharyngeal endotracheal tubes, and/or possibly other of oral, nasal, supraglottic type airway devices.

Most endotracheal tubes 2 or other airways of a narrower diameter are preferably handled like the drawings in FIG. 8 described above. The primary difference with FIG. 9 as compared to FIG. 8 is that the diameter of the airway device is so large that preferred embodiments of taping systems does not need to wrap it and allow the fourth wing 28 to still provide a desired anchor effect against the face for at least some embodiments (other embodiments could have longer wings to accommodate such airway devices). With tubes inserted into the nose, the third and/or fourth wing 26,28 may be wrapped around the tube (because of its small size) but it then may preferably be secured to either the cheek or the bridge of the nose (depending on practitioner preference and/or the location of surgery) on the face 7 of patient 9. This type of airway is used less frequently compared to oral tubes such as tube 2 and supraglottic airways 4, but preferred embodiments of the taping system (airway holder 30) accommodate other airways than those shown in the Figures.

Adhesive tape could possibly now disappear from the operating room, therefore removing a potential source of inadvertently spreading contamination from one patient to another in an unintended manner. Furthermore, kits such as kit 10 can be readily provided for specific applications whether the kit 10 contains a single airway holder 30, possibly eye patches 12,14 and/or multiple airway holders 30 and/or other components depending on the particular applications that preferably be designed for a single-patient and not multi-patient use.

Numerous alterations of the structure herein disclosed will suggest themselves to those skilled in the art. However, it is to be understood that the present disclosure relates to the preferred embodiment of the invention, which is for purposes of illustration only and not to be construed as a limitation of the invention. All such modifications which do not depart from the spirit of the invention are intended to be included within the scope of the appended claims.

What is claimed is:

1. An airway holder comprising:
a first pair of wings identified as first and second wings;
a second pair of wings identified as third and fourth wings;
a center portion where first and second pairs of wings connect;
wherein the first and second wings are symmetrically disposed about the center portion and more than half of the first and second wings are colinear; and all four wings have adhesive on a rear portion thereof, and
wherein the fourth wing extends away from the center portion and has an offset with an arm bending upwardly at an elbow and downwardly at a shoulder to then transition to a leg.

2. The airway holder of claim 1 wherein the first and second pairs of wings are initially coplanar with the center portion, and the adhesive on a rear portion of the first and second wings is initially provided against release paper.

3. The airway holder of claim 2 wherein the third and fourth wings have adhesive on a rear portion thereof and is initially provided against release paper.

4. The airway holder of claim 1 wherein the third wing has a leg.

5. The airway holder of claim 1 wherein the center portion has adhesive on a rear side thereof.

6. The airway holder of claim 5 wherein the center portion is configured to adhered to an airway device when in use.

7. The airway holder of claim 6 wherein the first wing is configured to adhered to the face of a patient when in use.

8. The airway holder of claim 7 wherein the second wing is configured to adhered to the face of a patient when in use.

9. The airway holder of claim 8 wherein a portion of the third wing is configured to adhered to the face of the patient when in use.

10. The airway holder of claim 9 wherein a portion of the fourth wing is configured to adhered to a portion of the airway device when in use.

11. The airway holder of claim 10 wherein the offset extends about a portion of the second wing and the airway device when in use.

12. The airway holder of claim 11 wherein a portion of the fourth wing connects to the face when in use.

13. The airway holder of claim 1 wherein the airway holder is provided as a portion of a kit with two eye patches.

14. The airway holder of claim 13 wherein the eye patches have a planar top edge.

15. The airway holder of claim 14 wherein a tab extends from the planar top edge for use in removal of the eye patches.

16. The airway holder of claim 13 wherein the eye patches have a curved bottom edge.

17. The airway holder of claim 13 wherein the eye patches have a tab extending from the bottom edge for use in installing the eye patches.

18. An airway holder comprising:
a first pair of wings identified as first and second wings;
a second pair of wings identified as third and fourth wings;
a center portion where first and second pairs of wings connect;
wherein the first and second wings are symmetrically disposed about the center portion;
and the third and fourth wings are asymmetrically disposed about the center portion, and
all four wings and the center portion have adhesive on a rear portion thereof, and
wherein the fourth wing extends away from the center portion and has an offset with an arm bending upwardly at an elbow and downwardly at a shoulder to then transition to a leg.

19. The airway holder of claim 18 wherein the offset spaces the leg of the fourth wing from the center portion.

* * * * *